| United States Patent [19] | [11] Patent Number: 5,041,548 |
| Sato et al. | [45] Date of Patent: * Aug. 20, 1991 |

[54] METHOD FOR THE PREPARATION OF TRIETHYLENE DIAMINES

[75] Inventors: Haruhito Sato; Masanori Tsuzuki, both of Sodegaura, Japan

[73] Assignee: Idemitsu Kosan Company Limited, Tokyo, Japan

[*] Notice: The portion of the term of this patent subsequent to Oct. 30, 2007, has been disclaimed.

[21] Appl. No.: 71,268

[22] PCT Filed: Dec. 3, 1986

[86] PCT No.: PCT/JP86/00614

§ 371 Date: Jun. 17, 1987

§ 102(e) Date: Jun. 17, 1987

[87] PCT Pub. No.: WO87/03592

PCT Pub. Date: Jun. 18, 1987

[30]  Foreign Application Priority Data

Dec. 5, 1985 [JP] Japan .................. 63-272490

[51] Int. Cl.⁵ .................. C07D 487/06; C07D 403/04; C07D 413/14
[52] U.S. Cl. ...................... 544/352; 544/82; 544/116

[58] Field of Search ............... 544/358, 352, 82, 116

[56]  References Cited

U.S. PATENT DOCUMENTS

| 2,977,363 | 3/1961 | Farkas et al. | 544/352 |
| 3,120,526 | 2/1964 | Brader | 544/352 |
| 3,956,329 | 5/1976 | Murakami et al. | 544/352 |
| 4,289,881 | 9/1981 | Imre et al. | 544/352 |
| 4,804,758 | 2/1989 | Hoelderich et al. | 544/352 |

FOREIGN PATENT DOCUMENTS

| 0158319 | 10/1985 | European Pat. Off. |  |
| 206896 | 2/1984 | German Democratic Rep. | 544/352 |
| 260574 | 12/1985 | Japan . |  |

*Primary Examiner*—John M. Ford
*Attorney, Agent, or Firm*—Frishauf, Holtz, Goodman & Woodward

[57]  ABSTRACT

Triethylene diamines are prepared in a high yield with an amine compound having a specific group as the starting material by bringing the same into contact with a catalyst formed of a crystalline metal silicate of which the molar ratio ($SiO_2/M_2O_3$) of silicon dioxide ($SiO_2$) to the oxide of a tervalent metal ($M_2O_3$, M being the tervalent metal) is at least 12. Particularly high efficiency can be obtained by using a crystalline metal silicate crystallized in the presence of an organic crystallizing agent.

22 Claims, No Drawings

METHOD FOR THE PREPARATION OF TRIETHYLENE DIAMINES

FIELD OF TECHNOLOGY

This invention relates to a method for the preparation of triethylene diamines or, more particularly, to a method for the preparation of triethylene diamines with good efficiency from an amine compound having, in the molecule, a group represented by the general formula

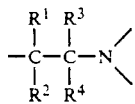

wherein, $R^1$, $R^2$, $R^3$ and $R^4$ each denote a hydrogen atom or an alkyl group having 1 to 4 carbon atoms by using a specific crystalline metal silicate as the catalyst.

BACKGROUND TECHNOLOGY

While, in the prior art, triethylene diamine was prepared from aminoethyl piperazine as the starting material, a method has been developed in recent years to give a high yield from hydroxyethyl piperazine as the starting material using a calcium phosphate-based catalyst (Japanese Patent Kokai 58-17839).

These starting compounds, however, are expensive with low availability so that the above described methods are not suitable for practice.

On the other hand, Japanese Patent Kokai 51-141895 discloses a method for the preparation of triethylene diamine by bringing diethanol amine as the starting material into contact with an alumina catalyst, silica-alumina catalyst or silica-alumina catalyst substituted by metal ions. This method, however, is a two-step process in which an intermediate is prepared in the course thereof and subsequently triethylene diamine is prepared and the yield is low in addition to the troublesomeness of the working procedure.

The present invention has an object to develop a method for the preparation of triethylene diamines in a simple procedure and still in a high yield by use of various kinds of readily available starting compounds overcoming the above described defects in the prior art technology.

DISCLOSURE OF INVENTION

Namely, the present invention provides a method for the preparation of triethylene diamines characterized, in the preparation of triethylene diamines by bringing an amine compound having, in the molecule, a group represented by the general formula

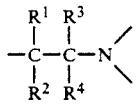  [I]

wherein, $R^1$, $R^2$, $R^3$ and $R^4$ each denote a hydrogen atom or an alkyl group having 1 to 4 carbon atoms into contact with a catalyst, by using, as the catalyst, a crystalline metal silicate, in which the molar ratio ($SiO_2/M_2O_3$) of silicon dioxide ($SiO_2$) to the oxide of a tervalent metal ($M_2O_3$, M denoting a tervalent metal) is at least 12, formed by the crystallization in the presence or in the absence of an organic crystallizing agent (excepting those crystallized in the absence of an organic crystallizing agent when the tervalent metal is aluminum alone).

The triethylene diamines of the present invention here implied are the compounds represented by the general formula

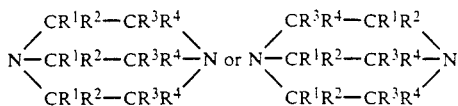

in the formula, $R^1$, $R^2$, $R^3$ and $R^4$ are the same as above defined.

THE BEST EMBODIMENT TO PRACTICE THE INVENTION

The starting compound used for practicing the method of the present invention may be any of the amine compounds having the group represented by the above given general formula [I] in the molecule including various compounds although it is usually monoethanol amine, isopropanol amine, diethanol amine, diisopropanol amine, triethanol amine, piperazine, N-hydroxyethyl piperazine, N-aminoethyl piperazine, morpholine, ethylene diamine, diethylene triamine, triethylene tetramine or the like.

The crystalline metal silicate used as the catalyst in the method of the present invention is a product by the crystallization in the presence or in the absence of an organic crystallizing agent, of which the crystalline skeleton is composed mainly of silicon dioxide ($SiO_2$) and an oxide of a tervalent metal ($M_2O_3$), while the proportion of them or, namely, $SiO_2/M_2O_3$ (molar ratio) should be at least 12 or, preferably, from 40 to 3000 or, more preferably, from 90 to 500. In this case, the $SiO_2/M_2O_3$ (molar ratio) smaller than 12 is undesirable due to the decrease in the yield of the triethylene diamines.

The crystalline metal silicate is obtained usually by the hydrothermal reaction of a silica source and a source of the trivalent metal and it is optional in this case that the crystallization is performed in the presence of an organic crystallizing agent. It should be noted here that, when the trivalent metal is aluminum alone or, namely, the crystals to be obtained are crystalline aluminosilicate, those crystallized in the presence of an organic crystallizing agent exhibit much better catalytic activity than those formed in the absence thereof. When the trivalent metal is not aluminum or aluminum is used in combination with other trivalent metals, however, even those crystallized in the absence of any organic crystallizing agent may exhibit satisfactory catalytic activity although excellent catalytic activity is exhibited by those crystallized in the presence of an organic crystallizing agent.

As the above mentioned organic crystallizing agent used in the forming process of the crystalline metal silicate are named tetraalkyl ammonium compounds of which the alkyl group has 2 to 5 carbon atoms, polyalkylene polyamines such as ethylene diamine, hexamethylene diamine and the like, amine compounds such as amino alcohols, morpholines and the like, amide compounds, diol compounds such as ethylene glycol and the like, pentaerithritol compounds, ether compounds such as diethyl ether, dioxane and the like, phenols, ketones, esters and so on, of which preferable are the tetraalkyl ammonium compounds of which the alkyl group has 2 to 5 carbon atoms or more preferable are tetrapropyl ammonium salts.

The crystalline metal silicate used in the method of the present invention may be any of those having the above mentioned $SiO_2/M_2O_3$ (molar ratio) without particular limitations in other respects although the preferable crystalline metal silicate should have a principal hollow made of a 10-membered ring of oxygen or, in particular, should belong to the class of the metal silicates of the pentasyl-type structure. Further, the tervalent metal (M) forming the crystalline metal silicate includes aluminum (Al), gallium (Ga), boron (B), iron (Fe), indium (In), lanthanum (La), scandium (Sc), yttrium (Y), chromium (Cr), titanium (Ti) and the like, of which one kind or two kinds or more of the metallic elements are named.

Particular examples of the crystalline metal silicates mentioned above include ZSM-5 described in U.S. Pat. No. 3,790,471 and other patent publications, ZSM-8 described in Japanese Patent Kokai 47-25097 and ZSM-11 described in Japanese Patent Publication 53-23280. In addition, the crystalline aluminosilicates such as ZSM-35 described in Japanese Patent Kokai 52-139029 and elsewhere, ZSM-21 described in U.S. Pat. No. 4,001,346 and other patent publications and the like can be used provided that $SiO_2/M_2O_3$ is 12 or larger.

Further, examples where M is B are given by the crystalline borosilicates having a ZSM-5 type structure or ZSM-11 type structure described in Japanese Patent Kokai 53-55500 or Japanese Patent Kokai 55-7598. Examples where M is Fe are given by the crystalline ferrosilicates such as ferrielite and the like described in Journal of Catalysis, volume 35, pages 256-272 (1974), Japanese Patent Kokai 50-127898, Japanese Patent Kokai 55-85415 and elsewhere. Examples where M is Ga are given by the crystalline gallosilicates such as the gallosilicates having a ZSM-5 type structure described in Reference Example 4 given later and others. Examples where M is In, La, Sc, Y, Cr, Ti, Be or Mn are given by the crystalline metal silicates having a structure in which the cations of Al built in the skeleton of the above mentioned crystalline aluminosilicate are replaced with the cations of In, La, Sc, Y, Cr, Ti, Be and Mn, respectively.

Among them, those in which the tervalent metal M is Al, Ga or B are preferable and those in which M is Al or Ga are more preferable.

As is described above, in the meantime, the presence of an organic crystallizing agent is essential when the tervalent metal is aluminum alone or, namely, the crystalline metal silicate is a crystalline aluminosilicate but not essential otherwise.

The above mentioned crystalline metal silicate used in the method of the present invention can be prepared by a known method.

For example, it is a known method of synthesis that the pentasyl type crystalline metal silicate represented by the above mentioned ZSM-5 type zeolite can be prepared by the hydrothermal synthesis using a mixture of which the principal ingredient is, for example, a salt or oxyacid salt, such as sulfates, nitrates and the like, of the metallic element M such as aluminum sulfate, gallium nitrate, boric acid, iron (III) sulfate, chromium sulfate, sodium aluminate and the like as the source of the metal oxide ($M_2O_3$) and silicic acid, composite thereof or silicate such as colloidal silica, water glass and the like as the silica source in the presence of an organic crystallizing agent.

Further, it is a known method of preparation that the above mentioned hydrothermal synthesis is performed in the coexistence of an alkali metal compound such as the hydroxide, halide and the like of an alkali metal such as sodium and the like.

The crystalline metal silicates obtained by these methods are usually not in the $H^+$ form but are substituted for the $H^+$ by quaternary ammonium ions and/or alkali metal ions such as $Na^+$ and the like so that conversion of them into the $H^+$ form is desirable. This exchange can easily be achieved by a known method.

For example, it is known that conversion of the quaternary ammonium ions into $H^+$ can be achieved by calcination in air at a temperature of 500° to 600° C. while, on the other hand, conversion of the alkali metal ions such as $Na^+$ and the like into $H^+$ is performed often by a method of obtaining a $H^+$ form crystalline metal silicate in which, for example, the crystalline metal silicate of the alkali metal salt form is converted by a treatment with an aqueous solution of an ammonium salt such as ammonium nitrate, ammonium chloride and the like into a crystalline metal silicate of the ammonium salt form which is then calcined in air at 300° to 600° C.

In addition to the above, usable method includes a direct treatment with a diluted acid such as a diluted hydrochloric acid.

Besides these, various methods are known as the synthetic method for the crystalline metal silicates.

The crystalline metal silicate used as the catalyst in the method of the present invention can be synthesized by any of these methods and the present invention is never limited to the use of a catalyst by a specific preparation method.

Although it is preferable in the present invention that the crystalline metal silicate is in the $H^+$ form, meanwhile, it is optional insofar as the object of this invention is not obstructed that a part or all of the $H^+$s in the catalyst are replaced with other cations such as magnesium ions, calcium ions, lanthanum ions and the like.

The solid catalyst of the present invention can be used in any form of powdery, granular, chip-like, spherical, pellet-like and other forms.

When the crystalline metal silicate is hydrothermally synthesized in the present invention by formulating an organic crystallizing agent, it is preferable that the above mentioned crystalline metal silicate is calcined prior to the reaction in a stream of air and/or an inert gas such as nitrogen and the like in order to enhance the catalytic activity.

Although, in this case, the conditions of calcination depend on the kind of the above mentioned crystalline metal silicate, remaining of the quaternary ammonium ions and structural water and so on, organic compounds in the metal silicate can be removed usually by heating for 1 hour or longer or, preferably, for 3 hours or longer at a temperature of 400° to 600° C. or, preferably, 450° to 550° C.

In the method of the present invention, the objective triethylene diamines can be obtained with high efficiency by the reaction of the amine compound having the group expressed by the above given general formula [I] in the molecule as the starting material using the crystalline metal silicate prepared in this manner as the catalyst. The reaction of this amine compound proceeds by bringing the amine compound into contact with the catalyst composed of the above described crystalline metal silicate and the reaction temperature should usually be selected from the range of 200° to 500° C. or, preferably, 250° to 450° C. although the conditions of the reaction temperature, pressure, time and the like in this case cannot be given definitely depending on the kind of the amine compound to be used, the kind of the crystalline metal silicate and so on.

And, the method of the reaction may be either batchwise or continuous and the reaction time in the batchwise method should be 10 minutes to 48 hours or, preferably, 1 to 10 hours while the WHSV (weight-space velocity) in the continuous reaction should be 0.1 to 100 hour$^{-1}$ or, preferably, 0.5 to 20 hour$^{-1}$.

In the method of the present invention, furthermore, it is optional that the reaction is performed by diluting the amine compound as the starting material with an inert gas such as hydrogen gas, nitrogen gas, water vapor, hydrocarbons and the like or an inert solvent such as water, inert hydrocarbons and the like.

Although these diluents can be used in any desired amount, it is preferable due to the increase in the yield of the triethylene diamines that the molar ratio of the amine compound as the starting material to the diluent should not exceed 1 in the case of a gas-phase reaction and the weight ratio of the amine compound as the starting material to the diluent should not exceed 1 in the case of a liquid-phase reaction.

In any case, the reaction can be performed under a spontaneously produced pressure at the reaction temperature or under pressurization and it is also an effective way in a batch-wise reaction that the reaction is performed while the triethylene diamines as the reaction product are continuously distilled away.

The amount of the crystalline metal silicate used in the method of the present invention as the catalyst is sufficient in a batch-wise reaction when it is in the range from 0.1 to 100% by weight or, preferably, from 1 to 10% by weight based on the amine compound as the starting material though dependent on the kind of the cataryst and the amine compound as the starting material of the reaction and other conditions.

After completion of the reaction, the catalyst is separated and removed in a procedure of solid-liquid separation followed by isolation and purification of the triethylene diamines by distillation or other method but, in a batch-wise reaction, the produced triethylene diamines may be taken out of the mixture merely by distillation usually without separation and removal of the catalyst. The unreacted amine compound recovered by this distillation procedure can be re-used as the starting material.

The crystalline metal silicate used as the catalyst in the method of the present invention can be used repeatedly as a highly active catalyst by timely performing a calcination treatment for regeneration.

In the following, the present invention is described in more detail with reference to the examples.

REFERENCE EXAMPLE 1

Preparation of crystalline aluminosilicate (I)

Solution A was prepared by dissolving 7.5 g of aluminum sulfate in 250 ml of water and then dissolving 17.6 g of concentrated sulfuric acid and 26.3 g of tetra-n-propyl ammonium bromide therein, Solution B was prepared by dissolving 211.0 g of water glass [J sodium silicate #3, manufactured by Nippon Kagaku Kogyo Co.] in 250 ml of water and Solution C was prepared by dissolving 79.0 g of sodium chloride in 122 ml of water.

In the next place, the above mentioned Solutions A and B were simultaneously added dropwise into Solution C at room temperature over a period of 10 minutes. The thus obtained mixed solution was introduced into an autoclave and subjected to a heat treatment at 170° C. for 20 hours. After cooling, the content was filtered and washed with water and then dried at 120° C. for 12 hours. The product could be identified by the X-ray diffractometric analysis to be ZSM-5. The thus obtained ZSM-5 was calcined at 550° C. for 6 hours to give 56.5 g of a sodium-form ZSM-5. This sodium-form ZSM-5 was added to 5 times by weight of a 1N aqueous solution of ammonium nitrate and heated under reflux for 8 hours. Thereafter, the mixture was cooled and kept standing and the supernatant was removed by decantation. Further, the procedure of refluxing and decantation was repeated three times and then the content was filtered, washed with water and calcined at 120° C. for 12 hours to give an ammonium-form ZSM-5. The SiO$_2$/Al$_2$O$_3$ thereof was 90 (molar ratio). This ammonium-form ZSM-5 was calcined in air at 550° C. for 4 hours to give an H-form ZSM-5, i.e. crystalline aluminosilicate (I).

REFERENCE EXAMPLE 2

Preparation of crystalline aluminosilicate (II)

The conditions for the preparation were entirely the same as in the preparation of the crystalline aluminosilicate (I) described in Reference Example 1 except that the formulated amount of aluminum sulfate was changed to 15.0 g to prepare the crystalline aluminosilicate (II). The SiO$_2$/Al$_2$O$_3$ thereof was 45 (molar ratio).

REFERENCE EXAMPLE 3

Preparation of crystalline aluminosilicate (III)

Solution A was prepared by dissolving 6.0 g of sodium aluminate and 4.6 g of sodium hydroxide in 105 ml of hot water, Solution B was prepared by dissolving 138.6 g of a colloidal silica in 466 ml of water and Solution B was added dropwise to Solution A.

In the next place, the thus obtained mixed solution was subjected to a heat treatment at 150° C. for 120 hours in an autoclave followed by the same subsequent treatment as in Reference Example 1 to give the crystalline aluminosilicate (III). The SiO$_2$/Al$_2$O$_3$ thereof was 45 (molar ratio).

REFERENCE EXAMPLE 4

Preparation of crystalline gallosilicate

Solution A was prepared by dissolving 2.34 g of gallium nitrate, 4.42 g of concentrated sulfuric acid and 6.58 g of tetra-n-propyl ammonium bromide in 62 ml of water, Solution B was prepared by dissolving 52.78 g of water glass [J sodium silicate #3, manufactured by Nippon Kagaku Kogyo Co.] in 62 ml of water and Solution C was prepared by dissolving 19.75 g of sodium chloride in 30 ml of water. Then, Solutions A and B were simultaneously added dropwise to Solution C. The thus obtained mixed solution was introduced into an autoclave to effect the reaction at a reaction temperature of 170° C. for 24 hours. After cooling, the content of the autoclave was filtered, washed with water and dried at 120° C. for 12 hours followed by calcination at 600° C.

for 6 hours to give 9.6 g of a sodium-form cristalline gallosilicate.

In the next place, the thus obtained gallosilicate was added to 5 times by weight of a 1N solution of ammonium nitrate, subjected to a heat treatment at 80° C. for 8 hours and, after cooling, filtered. Further, the solid material was subjected to three times repetition of a procedure of heating and filtration followed by washing with water and drying at 120° C. for 16 hours to give an ammonium-form crystalline gallosilicate of which the relative composition of $SiO_2$ and $Ga_2O_3$ was $SiO_2/Ga_2O_3=75.5$ (molar ratio). Further, the X-ray diffraction of this gallosilicate indicated that it had a structure of ZSM-5. This ammonium-form crystalline gallosilicate was calcined in air at 550° C. for 4 hours to give an H-form crystalline gallosilicate.

REFERENCE EXAMPLE 5

Preparation of crystalline borosilicate

Solution A was prepared by dissolving 2.54 g of boron oxide in 325 ml of water and then adding 73.32 g of concentrated sulfuric acid and 88.08 g of tetra-n-propyl ammonium bromide. Besides, Solution B was prepared by dissolving 686.14 g of water glass [trade name "J Sodium Silicate #3", manufactured by Nippon Kagaku Kogyo Co.] in 325 ml of water. Further, Solution C was prepared by dissolving 125.65 g of sodium chloride in 182 ml of water.

In the next place, Solutions A and B were simultaneously added dropwise into Solution C. The thus obtained mixed solution was introduced into an autoclave and subjected to a heat treatment at 170° C. for 20 hours. After cooling, the content was filtered, washed with water and dried at 120° C. for 12 hours followed by calcination at 550° C. for 6 hours to give 140.3 g of a sodium-form crystalline borosilicate.

The thus obtained borosilicate was added to 5 times by weight of a 1N aqueous solution of ammonium nitrate and, after 8 hours of refluxing and cooling, the supernatant was removed by decantation. Further, the procedure of refluxing and decantation was repeated three times and the content was filtered, washed with water and dried at 120° C. for 12 hours to give an ammonium-form borosilicate. The $SiO_2/B_2O_3$ (molar ratio) of the thus obtained ammonium-form borosilicate was 170. This ammonium-form borosilicate was calcined in air at 550° C. for 4 hours to give an H-form crystalline borosilicate.

REFERENCE EXAMPLE 6

Preparation of crystalline ferrosilicate

Solution A was prepared by dissolving 8.24 g of iron (III) nitrate in 250 ml of water and then adding 17.6 g of concentrated sulfuric acid and 26.3 g of tetra-n-propyl ammonium bromide. Besides, Solution B was prepared by dissolving 211.0 g of water glass [tradename "J Sodium Silicate #3", manufactured by Nippon Kagaku Kogyo Co.] in 250 ml of water. Further, Solution C was prepared by dissolving 79.0 g of sodium chloride in 122 ml of water.

On the base thereof, 48.2 g of a sodium-form ferrosilicate was obtained in the same manner as in the above described Reference Example 5 and an ammonium-form ferrosilicate, of which the $SiO_2/Fe_2O_3$ (molar ratio) was 100 was obtained, from which an H-form crystalline ferrosilicate was obtained.

EXAMPLE 1

A fixed-bed flow-reaction tube was filled with 2 g of the crystalline aluminosilicate (I) obtained in Reference Example 1 and, while the temperature was kept at 400° C., a mixture of monoethanolamine and water (weight ratio of monoethanolamine/water = ¼) was introduced under a condition of WHSV 10 hour$^{-1}$. As a result thereof, triethylene diamine was obtained in a yield of 63.5%. Besides, 11.3% of the monoethanol amine as the starting material was recovered as the unreacted starting material.

EXAMPLE 2

The same procedure as in Example 1 was performed except that the WHSV and temperature in Example 1 were changed to 2 hour$^{-1}$ and 350° C., respectively. As a result thereof, triethylene diamine was obtained in a yield of 65.7% and 7.5% of the unreacted starting material was recovered.

EXAMPLE 3

The same procedure as in Example 1 was performed except that the crystalline aluminosilicate (II) obtained in Reference Example 2 was used in place of the crystalline aluminosilicate (I) in Example 1. As a result thereof, triethylene diamine was obtained in a yield of 53.0%. Besides, 6.2% of the unreacted starting material was recovered.

EXAMPLE 4

A fixed-bed flow-reaction tube was filled with 2 g of the crystalline aluminosilicate (II) obtained in Reference Example 2 and, while the temperature was kept at 350° C., a mixture of monoethanol amine and water (weight ratio ¼) was introduced under a condition of WHSV 6.4 hour$^{-1}$. As a result thereof, triethylene diamine was obtained in a yield of 51.4% and 31.3% of the unreacted starting material was recovered.

EXAMPLE 5

The same procedure as in Example 4 was performed except that the monoethanol amine in Example 4 was replaced with N-hydroxy ethyl piperazine and the WHSV was changed to 6.9 hour$^{-1}$. As a result thereof, triethylene diamine was obtained in a yield of 65.6% and 11.1% of the unreacted starting material was recovered.

COMPARATIVE EXAMPLE 1

The same procedure as in Example 4 was performed except that the crystalline aluminosilicate (III) obtained in Reference Example 3 was used in place of the crystalline aluminosilicate (II) in Example 4. As a result thereof, triethylene diamine was obtained in a yield of 1.0% and 97.8% of the unreacted starting material was recovered.

COMPARATIVE EXAMPLE 2

The same procedure as in Example 5 was performed except that the crystalline aluminosilicate (III) obtained in Reference Example 3 was used in place of the crystalline aluminosilicate (II) in Example 5. As a result thereof, triethylene diamine was obtained in a yield of 7.1% and 88.3% of the unreacted starting material was recovered.

Table 1 shows the results of the above described Examples 4 and 5 and Comparative Examples 1 and 2.

TABLE 1

| No. | Starting amine compound | Yield of triethylene diamine, % | Recovery of unreacted starting material, % |
| --- | --- | --- | --- |
| Example 4 | Monoethanol amine | 51.4 | 31.3 |
| Comparative Example 1 | Monoethanol amine | 1.0 | 97.8 |
| Example 5 | N-Hydroxy ethyl piperazine | 65.6 | 11.1 |
| Comparative Example 2 | N-Hydroxy ethyl piperazine | 7.1 | 88.3 |

(note) The crystalline aluminosilicate used in Comparative Examples 1 and 2 is a product by the crystallization in the absence of an organic crystallizing agent.

EXAMPLE 6

The same procedure as in Example 1 was performed except that the crystalline gallosilicate obtained in Reference Example 4 was used in place of the crystalline aluminosilicate (I) in Example 1. As a result thereof, triethylene diamine was obtained in a yield of 47.8% and 13.1% of the unreacted starting material was recovered.

EXAMPLE 7

The same procedure as in Example 6 was performed except that the crystalline borosilicate obtained in Reference Example 5 was used in place of the crystalline gallosilicate in Example 6. As a result thereof, triethylene diamine was obtained in a yield of 32.0% and 41.5% of the unreacted starting material was recovered.

EXAMPLE 8

The same procedure as in Example 6 was performed except that the crystalline ferrosilicate obtained in Reference Example 6 was used in place of the crystalline gallosilicate in Example 6. As a result thereof, triethylene diamine was obtained in a yield of 20.2% and 59.1% of the unreacted starting material was recovered.

EXAMPLES 9 TO 14

The same procedure as in Example 1 was performed except that the monoethanol amine in Example 1 was replaced with one of the amine compounds indicated in Table 2. The results thereof are shown in Table 2.

TABLE 2

| No. | Starting amine compound | Yield of triethylene diamine, % | Recovery of unreacted starting material, % |
| --- | --- | --- | --- |
| Example 9 | Diethanol amine | 30.2 | 7.5 |
| Example 10 | Piperazine | 55.6 | 36.0 |
| Example 11 | Morpholine | 32.6 | 9.1 |
| Example 12 | Ethylene diamine | 43.9 | 20.4 |
| Example 13 | Hydroxyethyl piperazine | 70.0 | 24.7 |
| Example 14 | Aminoethyl piperazine | 58.3 | 33.2 |

EXAMPLE 15

The same procedure as in Example 6 was performed except that the monoethanol amine in Example 6 was replaced with N-aminoethyl piperazine. As a result thereof, triethylene diamine was obtained in a yield of 34.2% and 35.7% of the unreacted starting material was recovered.

POSSIBILITY OF INDUSTRIAL APPLICATION

As is described above, various kinds of amine compounds can be used as the starting material according to the method of the invention and further the desired triethylene diamines can be prepared in a one-step reaction without intermediates. Besides, in the method of the present invention, the crystalline metal silicate used therein has excellent thermal stability and can be used at a relatively high temperature to give a possibility of maintaining a sufficiently high reaction velocity with the activity sustainedly exhibited over a long period of time and, in addition, it can be used repeatedly as the catalyst with high efficiency by being subjected to a regeneration treatment so that an industrially very advantageous method is provided with decreased production costs in comparison with the prior art methods.

Further, the triethylene diamines obtained by the method of the present invention are utilizable efficiently as a catalyst for foaming polymerization of polyurethane foams, curing agent of epoxy resins, polymerization catalyst of acrylonitrile and so on.

We claim:

1. A method for the preparation of triethylene diamines comprising contacting an amine compound having, in the molecule, a group represented by the formula

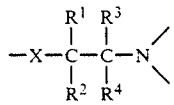

wherein $R^1$, $R^2$, $R^3$ and $R^4$ are independently a hydrogen atom or an alkyl group having 1 to 4 carbon atoms and X is an oxygen atom or a nitrogen atom
with a catalyst comprising a crystalline metal silicate formed by crystallization in the presence of an organic crystallizing agent, and having a molar ratio of silicon dioxide to $M_2O_3$ of at least 12 to 1 and wherein M is a tervalent metal, said amine compound is monoethanol amine, isopropanol amine, diethanol amine, diisopropanol amine, triethanol amine, piperazine, N-hydroxyethyl piperazine, N-aminoethyl piperazine, morpholine, ethylene diamine, diethylene triamine or triethylene tetramine, and said organic crystallizing agent is ethylene diamine, hexamethylene diamine, an amino alcohol, a morpholine, ethylene glycol, a pentaerithritol, diethyl either, dioxane, a phenol, a ketone, an ester or a tetraalkyl ammonium compound wherein the alkyls are $C_2$–$C_5$ alkyls.

2. A method for the preparation of triethylene diamines comprising contacting an amine compound having, in the molecule, a group represented by the formula

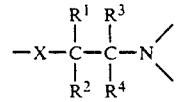

wherein $R^1$, $R^2$, $R^3$ and $R^4$ are independently a hydrogen atom or an alkyl group having 1 to 4 carbon atoms and X is an oxygen atom or a nitrogen atom with a catalyst comprising a crystalline metal silicate formed by crystallization in the presence of an organic crystallizing agent, and having a molar ratio of silicon dioxide to $M_2O_3$ of at least 12 to 1 and wherein M is a tervalent metal, which is a kind or two kinds or more of the metals selected from the group consisting of aluminum, gallium, boron, iron, indium, lanthanum, scandium, yttrium, chromium and titanium; and said amine compound is monoethanol amine, isopropanol amine, diethanol amine, diisopropanol amine, triethanol amine, piperazine, N-hydroxyethyl piperazine, N-aminoethyl piperazine, morpholine, ethylene diamine, diethylene triamine or triethylene tetramine.

3. The method of claim 2 wherein the crystalline metal silicate is crystalline alumino silicate.

4. The method of claim 3 wherein the organic crystallizing agent is the tetralkyl ammonium compound wherein the alkyls are $C_2$–$C_5$ alkyls.

5. The method of claim 4 wherein the organic crystallizing agent is the tetrapropyl ammonium salt.

6. The method of claim 2, wherein the organic crystallizing agent is one selected from the group consisting of tetraalkyl ammonium compound, polyalkylene polyamine, amine compound, amide compound, diol compound, pentaerithritol compound, ether compound, phenol compound, ketone and ester.

7. The method of claim 6 wherein the amine compound is monoethanol amine.

8. The method of claim 2, wherein the organic crystallizing agent is one selected from the group consisting of ethylene diamine, hexamethylene diamine, amino alcohol, morpholine, ethylene glycol, pentaerithritol, diethyl ether, dioxane, phenol and tetraalkyl ammonium compound of which the alkyl group has 2 to 5 carbon atoms.

9. The method of claim 8, wherein the amine compound is monoethanol maine.

10. The method of claim 2, wherein the amine compound is monoethanol amine.

11. A method for the preparation of triethylene diamines comprising contacting an amine compound having, in the molecule, a group represented by the formula

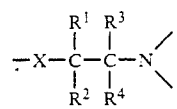

wherein $R^1$, $R^2$, $R^3$ and $R^4$ are independently a hydrogen atom or an alkyl group having 1 to 4 carbon atoms and X is an oxygen atom or a nitrogen atom, with a catalyst comprising a crystalline metal silicate having a molar ratio of silicon dioxide to $M_2O_3$ of at least 12 to 1 wherein M is a tervalent metal which is a kind or two kinds or more of the metals selected from the group consisting of aluminum, gallium, boron, iron, indium, lanthanum, scandium, yttrium, chromium and titanium; and said amine compound is monoethanol, amine, isopropanol amine, diethanol amine, diisopropanol amine, triethanol amine, piperazine, N-hydroxyethyl piperazine, N-aminoethyl piperazine, morpholine, ethylene diamine, diethylene triamine or triethylene tetramine.

12. The method of claim 11 wherein M is aluminum.

13. The method of claim 11 wherein M is gallium.

14. The method of claim 11 wherein M is boron.

15. The method of claim 11 wherein M is iron.

16. The method of claim 11 wherein M is indium.

17. The method of claim 11 wherein M is lanthanum, scandium or yttrium.

18. The method of claim 11 wherein M is chromium.

19. The method of claim 11 wherein M is titanium.

20. The method of claim 2 wherein the organic crystallizing agent is ethylene diamine or hexamethylene diamine.

21. The method of claim 2 wherein the organic crystallizing agent is ethylene glycol.

22. The method of claim 2 wherein the organic crystallizing agent is diethyl ether or dioxane.

* * * * *